(12) United States Patent
Rowlandson (10) Patent No.: US 7,076,287 B2
(45) Date of Patent: Jul. 11, 2006

(54) SYSTEM AND METHOD FOR DETECTING NEW LEFT BUNDLE BRANCH BLOCK FOR ACCELERATING TREATMENT OF ACUTE MYOCARDIAL INFARCTION

(75) Inventor: G. Ian Rowlandson, Milwaukee, WI (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 1147 days.

(21) Appl. No.: 09/751,024

(22) Filed: Dec. 29, 2000

(65) Prior Publication Data

US 2002/0087055 A1 Jul. 4, 2002

(51) Int. Cl.
*A61B 5/04* (2006.01)

(52) U.S. Cl. .................................... 600/509
(58) Field of Classification Search ............... 600/508, 600/509, 515–523; 370/392; 424/94.2; 128/903, 920, 904; 725/67
See application file for complete search history.

(56) References Cited

U.S. PATENT DOCUMENTS

| | | | | |
|---|---|---|---|---|
| 3,114,019 A | | 12/1963 | Koda | 200/87 |
| 4,030,486 A | | 6/1977 | Eastman | 128/2.06 R |
| 4,802,008 A | * | 1/1989 | Walling | 725/67 |
| 5,051,264 A | * | 9/1991 | Ambrus | 424/94.2 |
| 5,502,726 A | * | 3/1996 | Fischer | 370/392 |
| 6,230,048 B1 | * | 5/2001 | Selvester et al. | 600/523 |
| 6,564,090 B1 | * | 5/2003 | Taha et al. | 600/509 |

FOREIGN PATENT DOCUMENTS

| WO | WO 00/15098 | 3/2000 |
|---|---|---|
| WO | WO 00/44378 | 8/2000 |

* cited by examiner

*Primary Examiner*—George Manuel
(74) *Attorney, Agent, or Firm*—Ostrager Chong Flaherty & Broitman P.C.

(57) ABSTRACT

A system and a method for automatically detecting a new left bundle branch block (LBBB) in an ECG series and then issuing an alert for the purpose of accelerating treatment for acute myocardial infarction. A serial comparison program is used to compare each current ECG with a previous ECG for the same patient. Diagnostic statements, measurements and waveforms are compared and based on the comparisons, the system is able to automatically determine that the patient has a new LBBB. The system then automatically determines whether the patient belongs to the category of patients having a high probability of acute myocardial infarction. If acute myocardial infarction is suspected, the system generates a diagnostic statement stating that the new left bundle branch block may be due to acute myocardial infarction. The current ECG exhibiting a new LBBB is then identified with a special tag and sent to a central database server. The special tag enables the central database server to perform special routing of that record, e.g., via facsimile or digital pager, to alert on-call medical personnel to the need for immediate treatment.

16 Claims, 8 Drawing Sheets

SYSTEM AND METHOD FOR DETECTING NEW LEFT BUNDLE BRANCH BLOCK FOR ACCELERATING TREATMENT OF ACUTE MYOCARDIAL INFARCTION

FIELD OF THE INVENTION

This invention relates to the acquisition, analysis and routing electrocardiograms (ECGs) and other physiological data. In particular, the invention relates to automated monitoring of acquired ECGs to detect characteristics indicating a specific cardiovascular condition requiring accelerated treatment.

BACKGROUND OF THE INVENTION

In hospitals or other health-care settings, it is frequently necessary to observe critical physiological conditions of a patient, including cardiovascular conditions. Cardiovascular condition data is obtained from sensors applied to a patient, or by imaging and sensing devices. Further, cardiovascular data may be data reported by a cardiologist based on review of a patient or a patient's monitor or image data. Hospitals or health-care centers often have hundreds or even thousands of sensor and metering devices and hundreds or even thousands of cardiac patients that require monitoring periodically over a lifetime. This data may be stored in a database for archival functions and later retrieval.

A known ECG management system, the MUSE® (Marquette Universal System for Electrocardiography) system of GE Marquette Medical Systems, Inc., is a software-based product that runs on off-the-shelf hardware. In particular, this ECG management system comprises a database of ECGs plus applications software. The MUSE® system receives ECG data from a multiplicity of instruments via a plurality of networks, analyzes that ECG data using various programs such as a serial comparison program, generates reports containing the results of the analysis, and then routes those reports to various systems and peripheral devices. In particular, the MUSE® system has automatic report routing which can send reports to multiple devices, including a facsimile machine as well as a digital pager.

In the known system, each ECG received by the MUSE® system has been analyzed by the instrument which acquired the ECG. Each instrument incorporates ECG analysis programs such as 12SL® from GE Marquette Medical Systems, Inc., which is a computer program for analyzing simultaneously acquired 12-lead ECGs. The 12SL® program makes precise measurements of recorded cardiac signals, and then provides an interpretation of the ECG waveforms using ECG interpretation criteria for both rhythm and morphology. This generates diagnostic statements. The ECG information stored by MUSE® system contains waveforms, measurements and diagnostic statement. The serial comparison program uses all of these. It can also re-measure the waveforms and recalculate measurements and criteria. The serial comparison program can do this on both the current and previous ECG.

A program's accuracy is directly dependent upon the quality of the signal it acquires. In 1979, Marquette introduced an electrocardiograph that simultaneously acquired all of the leads from the 12-lead electrocardiogram. Prior to this time, all commercially available electrocardiographs could only acquire 3 leads at a time. Simultaneous recording was adopted so that the computer could use all signals from all 12 leads to properly detect and classify each QRS complex. The program also applies digital filters which remove power line noise and baseline sway.

Computer measurement of features within the QRS complex is very susceptible to artifact. In addition to filtering, there is another method of eliminating noise from the QRS complex: signal averaging. Instead of analyzing a single QRS complex, the Marquette 12SL® program generates a median complex. That is, it aligns in time, all of the QRS complexes of the same shape; it then generates a representative complex from the median voltages that are found at each successive sample time. This is more complicated than an average, but the method results in a cleaner signal since it disregards outliers.

All ECG computer programs are composed of two parts: one which measures the waveforms, the other which does the interpretation based on these measurements. The main task of the measurement section is to find the location of the major reference points (that is, the onsets and offsets of the P, QRS and T complexes). Consistent with the signal processing portion of the 12SL® program, the onsets and offsets of the major waves are delineated by an analysis of the slopes in all 12 simultaneous leads. That is, QRS duration is measured from the earliest onset in any lead to the latest deflection in any lead. Similarly, the QT interval is measured from the earliest detection of depolarization in any lead to the latest detection of re-polarization in any lead.

After the onsets and offsets of the P, QRS, and T complexes have been demarcated, the waves within each complex are measured according to published standards. These amplitudes and durations result in a measurement matrix containing more than 1600 values. This is then passed to the criteria portion of the 12SL® program so that it can generate an interpretation, including diagnostic statements referenced via a statement library.

The MUSE® system stores ECGs in such a fashion that they can be re-analyzed by the 12SL® program. That is, the fidelity of the stored ECG is such that it can be used as if it were freshly acquired from the patient.

Computerized electrocardiography has resulted in two practical advantages for the overreading physician. First, the computer serves as an additional expert opinion. Second, it is possible for cardiologists to overread computer-analyzed tracings in half the time required for conventional, non-analyzed ECGs. Therefore, the computer is not only used to efficiently record, store, transmit, and present the ECG—it is also used to assist the physician in overreading the ECG.

Marquette's serial comparison program helps reduce the number of unnecessary admissions to coronary care units (CCUs) by speeding the evaluation of "questionable" or "borderline" ECGs. The program, which runs on the MUSE® system, compares a patient's current ECG with previous ECGs. The technique of comparing the current ECG to the previous ECG of a patient is termed serial electrocardiography. Serial electrocardiography is used to identify changes in the patient's electrocardiogram. The Marquette serial comparison program was developed to use statements, ECG measurements and waveform comparison techniques to maximize performance and accuracy in the detection of clinically significant changes in rhythm, P, QRS, ST and T waves. The Marquette MUSE® system, which stores ECGs with physician-edited interpretations to both individual ECGs and serial comparisons, in tandem with the serial comparison program, allows for accurate and expedient processing of a patient's ECG data. It completes the comparison within minutes, and returns the report while the patient is still in the emergency room. Serial comparison saves time and money by promptly providing diagnostically useful information that helps reduce unneeded CCU admissions.

Serial comparison can provide a quick evaluation of many difficult-to-interpret ECG features, including the borderline Q waves of possible myocardial infarction, the mild ST segment elevation of possible myocardial injury and moderate ST segment elevation with Q-wave evidence of myocardial infarction, which may be persistent change resulting from old infarction. The precise, computerized comparison helps the physician to determine whether the patient has experienced an infarction, whether it is old or new, or whether the ECG reflects a variation that is normal for that patient.

Serial comparison is extremely quick and easy to use. The ECG in question is transmitted from the acquiring electrocardiograph to the MUSE® system using an automatic request for serial comparison of the patient's current and past ECGs. (The MUSE® system automatically stores a patient's successive ECGs.) Within minutes, the physician receives a serial comparison report, including previous ECGs, so that the physician can make his/her own visual comparisons.

It is normal to have significant day-to-day variation in the ECG waveform, and an ECG management system must be able to discriminate between normal and clinically significant variations. Certain clinical conditions can only be reliably detected via a serial analysis. The serial comparison program can detect a new left bundle branch block (LBBB) in an ECG series. It does this based on the ECG interpretation as well as direct comparison of the waveforms.

Acute myocardial infarction (a heart attack) is the leading cause of death in the United States of America. Acute myocardial infarction is often detected through serial change. The pertinent clinical changes in the ECG waveform include a small change in the so-called ST segment and a small new Q wave. These changes in the ECG waveform are typical of the evolution of acute myocardial infarction and must be detected in the face of normal variation.

Treatment via thrombolytic therapy (involving dissolution of a thrombus in an artery or the heart) is now indicated if a patient has a new LBBB in the presence of symptoms associated with acute myocardial infarction. The outcome for a patient with this clinical scenario is excellent, even superior to an acute myocardial infarction that only exhibits ST elevation. But time-to-treatment is critical during acute myocardial infarction. This cardiovascular change must be quickly identified and treatment must be immediately applied. There is little benefit in applying treatment when the elapsed time from the onset of chest pain to treatment exceeds 6 hours.

There is a need for a system and a method for providing early detection of a new LBBB in an ECG waveform in the presence of symptoms associated with acute myocardial infarction.

SUMMARY OF THE INVENTION

The present invention is directed to a system and a method for automatically detecting a new left bundle branch block (LBBB) in an ECG series and then issuing an alert for the purpose of accelerating treatment for acute myocardial infarction.

In accordance with the preferred embodiments, a serial comparison program is used to compare each current ECG record with a previous ECG record for the same patient. First, the diagnostic statements for the two ECG records are compared. If both ECG records exhibit LBBB, then no change is stated, i.e., the detected LBBB is not new. However, if only the current ECG record includes a diagnostic statement indicating LBBB, then the algorithm proceeds to the next step. In this next step, measurements related to LBBB criteria are compared. If changes of a predetermined percentage are not present, then no change is stated. If changes of a predetermined percentage are present, then the algorithm compares the ECG waveforms for the current and previous ECG records using cross correlation. If the change in the current waveform is less than a predetermined percentage, e.g., less than 25%, then no change is stated. Conversely, if the change in the current ECG waveform, compared to the previous ECG waveform, is greater than 25%, then a change will be stated.

The system then automatically determines whether the patient belongs to the category comprising patients identified to have a high probability of acute myocardial infarction. If acute myocardial infarction is suspected, the system generates a diagnostic statement stating that the new left bundle branch block may be due to acute myocardial infarction. The current ECG record exhibiting a new LBBB is then identified with a special tag and sent to a central database server. The special tag enables the central database server to perform special routing of that record, e.g., via facsimile or digital pager, to alert on-call medical personnel to the need for immediate treatment.

In accordance with one preferred embodiment of the invention, a method for monitoring a patient for the presence of a new left bundle branch block comprises the steps of acquiring current and previous electrocardiogram records at different times for a particular patient; determining that the patient has a new left bundle branch block based on an automated comparison of data in the current and previous electrocardiogram records; automatically detecting that the patient belongs to a category of patients having a high probability of acute myocardial infarction; and automatically generating a diagnostic statement stating that the new left bundle branch block may be due to acute myocardial infarction.

In accordance with a further preferred embodiment of the invention, a method for monitoring a patient for the presence of a new left bundle branch block comprises the steps of acquiring current and previous electrocardiogram records at different times for a particular patient; determining that the patient has a new left bundle branch block based on an automated comparison of data in the current and previous electrocardiogram records; automatically detecting that the patient belongs to a category of patients having a high probability of acute myocardial infarction; and automatically tagging said current electrocardiogram record with a special tag.

In accordance with another preferred embodiment of the invention, a system for monitoring a patient for the presence of a new left bundle branch block comprises: memory for storing a previous electrocardiogram record; an instrument for acquiring a current electrocardiogram record at a time which is later than the time when the previous electrocardiogram record was acquired; and a computer programmed to perform the following steps: determining whether a new left bundle branch block is present in a patient based on a comparison of data in the current and previous electrocardiogram records; detecting whether the patient belongs to a category comprising patients having a high probability of acute myocardial infarction, this detecting step being performed if a determination has been made that a new left bundle branch block is present; and generating a diagnostic statement stating that the new left bundle branch block may be due to acute myocardial infarction, this generating step being performed if patient is in the aforementioned high-risk category.

In accordance with a further preferred embodiment of the invention, a system for monitoring a patient for the presence of a new left bundle branch block comprises: memory for storing a previous electrocardiogram record; an instrument for acquiring a current electrocardiogram record at a time which is later than the time when the previous electrocardiogram record was acquired; and a computer programmed to perform the following steps: determining whether a new left bundle branch block is present in a patient based on a comparison of data in the current and previous electrocardiogram records; detecting whether the patient belongs to a category comprising patients having a high probability of acute myocardial infarction, this detecting step being performed if a determination has been made that a new left bundle branch block is present; and tagging the current electrocardiogram record with a special tag, this tagging step being performed if patient is in the aforementioned high-risk category.

In accordance with another preferred embodiment of the invention, a system for monitoring the condition of patients in a coronary care unit, emergency department or chest pain clinic comprises a local area network, a plurality of bedside monitors connected to the local area network, a computer connected to the bedside monitors via the local area network, and a central database containing electrocardiogram records which are accessible to the computer. Each of the bedside monitors comprises a plurality of leads coupled to a respective patient. The computer is programmed to perform the following steps: receiving from the central database a previous electrocardiogram record for a patient in the coronary care unit, emergency department or chest pain clinic; receiving a current electrocardiogram record for that same patient from one of the bedside monitors via the local area network; determining that a new left bundle branch block is present in the patient based on a comparison of data in the current and previous electrocardiogram records; and generating an alert that the new left bundle branch block may be due to acute myocardial infarction.

In accordance with another preferred embodiment of the invention, a method of treating a patient suspected to have acute myocardial infarction, comprising the following steps: admitting a patient to a coronary care unit, emergency department or chest pain clinic; monitoring that patient to acquire a current electrocardiogram record; receiving from a central database a previous electrocardiogram record for that patient; determining that the patient has new left bundle branch block based on a comparison of data in the current and previous electrocardiogram records; generating an alert that the new left bundle branch block may be due to acute myocardial infarction; and treating the patient in response to the alert.

Other features and aspects of the invention are described and claimed below.

DETAILED DESCRIPTION OF THE PREFERRED EMBODIMENTS

Figure 1:
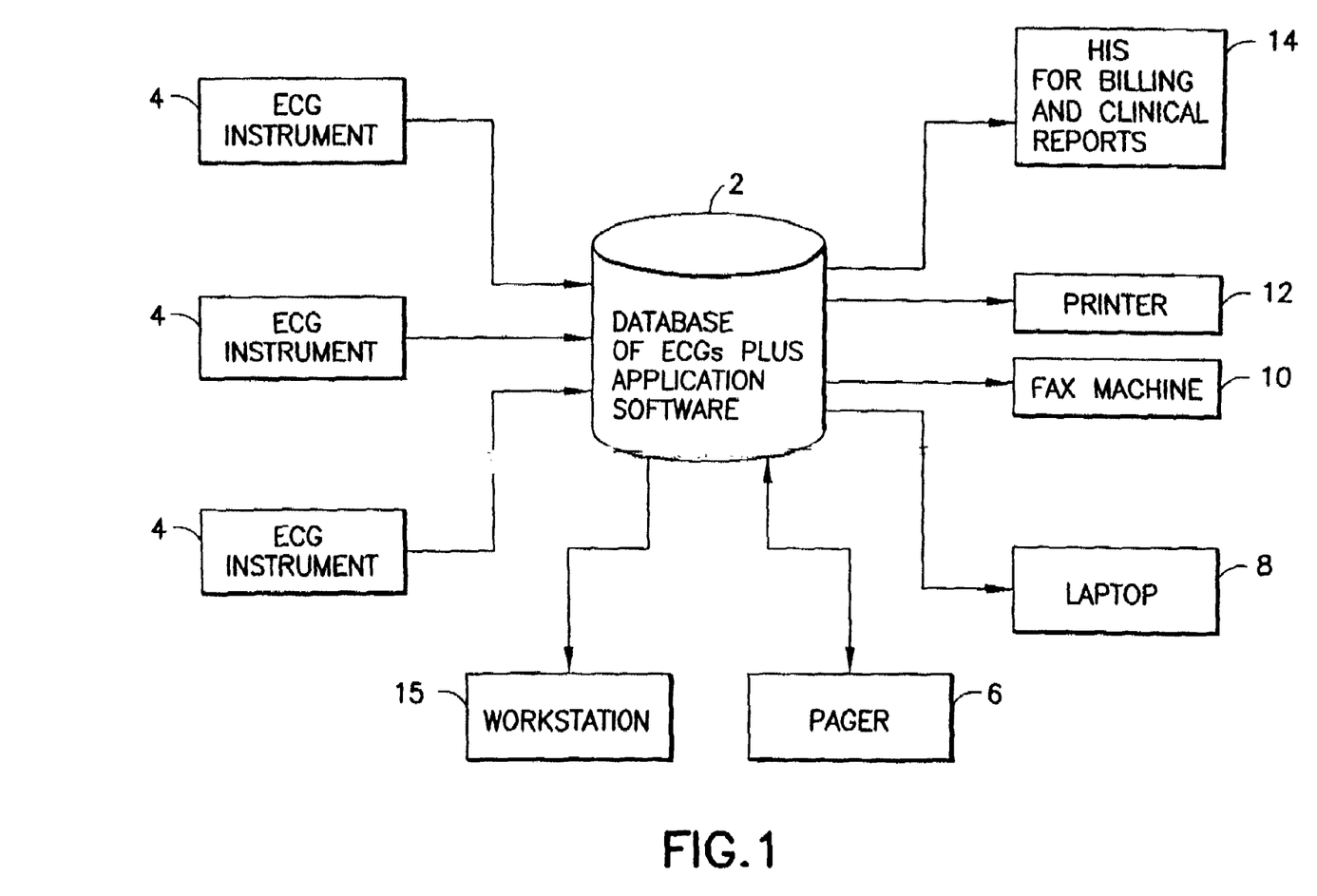
FIG. 1 is a block diagram showing a cardiovascular information system for acquiring, analyzing and routings ECGS.

Referring to FIG. 1, the MUSE® ECG management system 2 comprises a database of ECGs and applications software. The software is executed by a conventional server which communicates with a TCP/IP network. The ECGs are stored in a suitable storage medium which is accessible by the server. Any other suitable computer hardware may be used. The MUSE® system 2 receives ECG data from a multiplicity of instruments 4 via a plurality of networks, analyzes that ECG data using various programs such as the serial comparison program, generates reports containing the results of the analysis, and then routes those reports to various systems and peripheral devices. In particular, the MUSE® system has automatic report routing which can send reports to a digital pager 6, a laptop computer 8 (via email), a fax machine 10, a printer 12, a hospital information system 14 for billing and clinical reports, a workstation 15, and other servers on the local area network to which the MUSE® system is connected.

Figure 2:
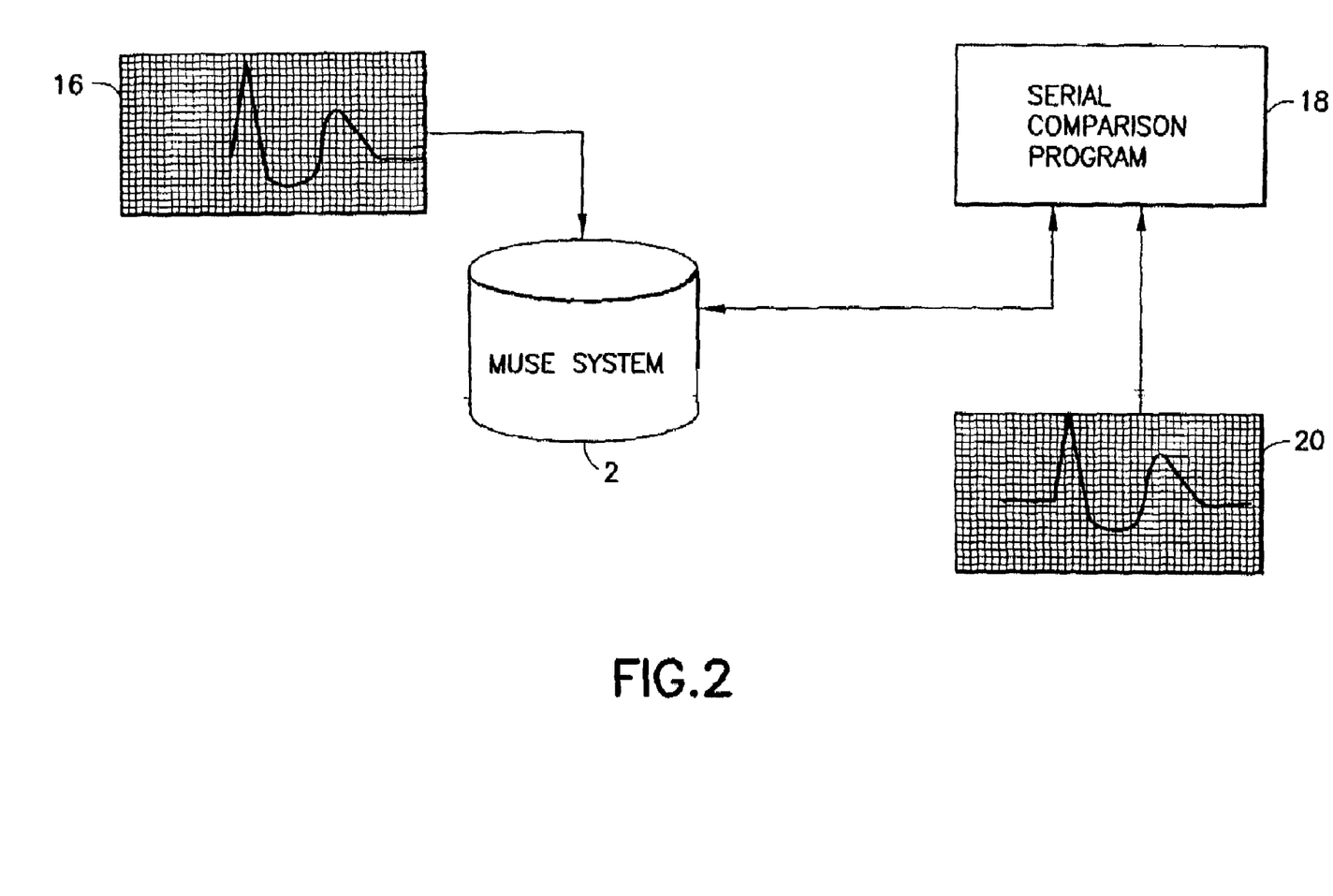
FIG. 2 is a flowchart showing a step performed by a serial comparison program incorporated in the cardiovascular information system shown in FIG. 1.

The applications software of the MUSE® system 2 comprises the previously described serial comparison program 18 (see FIG. 2). The current ECG 16 for a particular patient is acquired by the MUSE® system 2. This newly acquired ECG launches the serial comparison program 18. The serial comparison program 18 retrieves the record for the previous ECG 20 for the particular patient and renders it for comparison with the record for the current ECG for that same patient.

Figure 3:
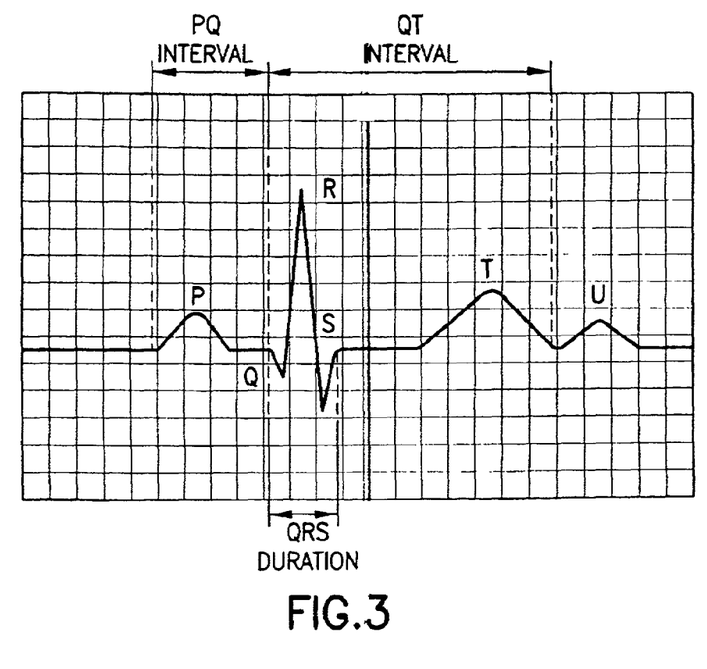
FIGS. 3 and 4 are graphs showing conventional ECG nomenclature.
Figure 4:
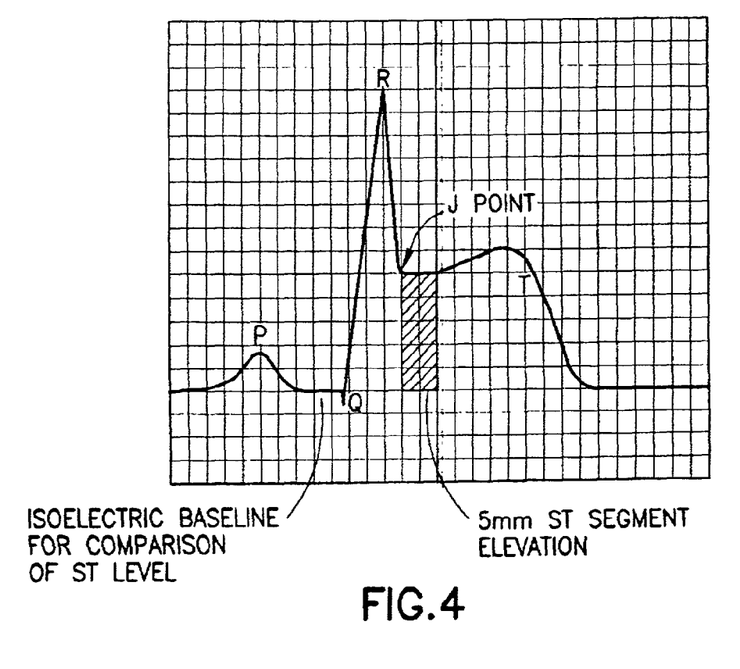
Figure 5:
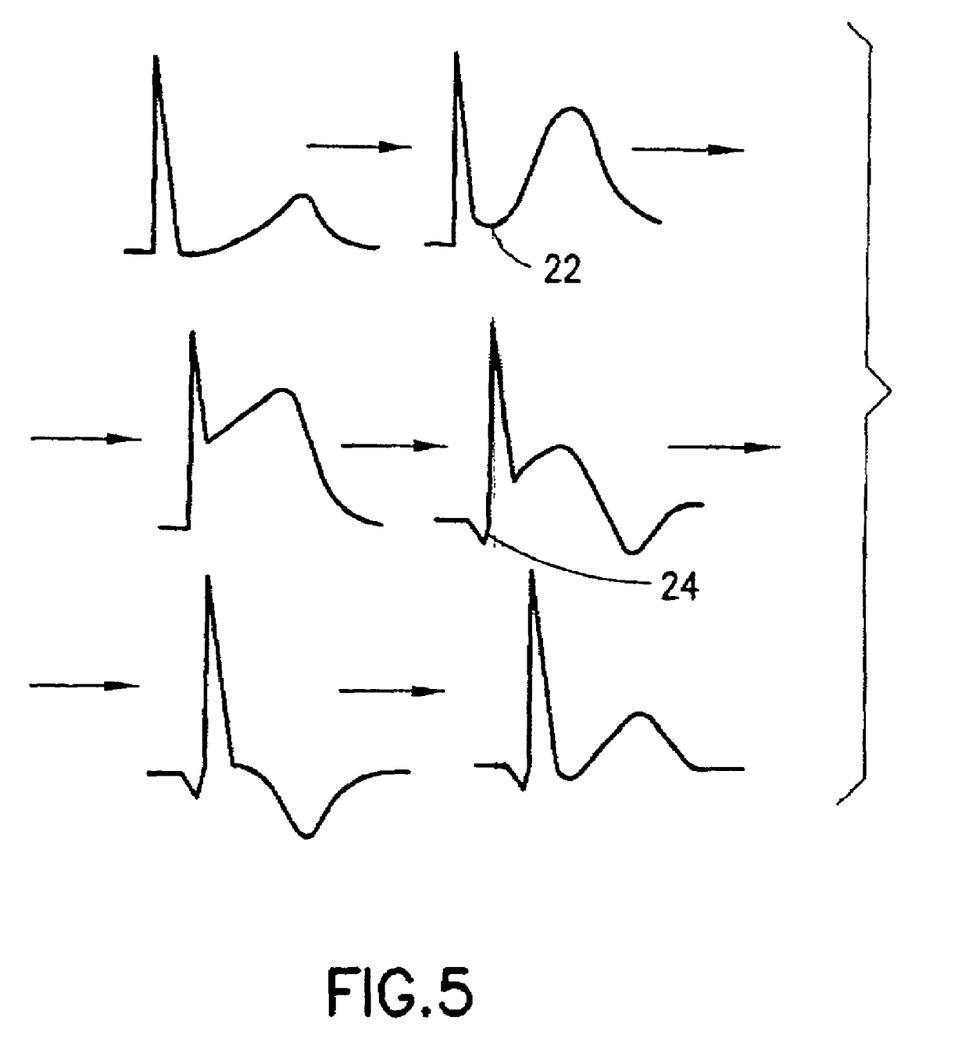
FIG. 5 is a schematic showing a typical sequence of ECG waveforms during evolution of an acute myocardial infarction.

The shape of a typical ECG waveform is shown in FIG. 3. The standard nomenclature identifies a P wave, a QRS complex, a T wave, and a U wave. The interval from the onset of the QRS complex to the end of the T wave is referred to as the QT interval. In FIG. 3, the ST segment is shown at the same height as the isoelectric baseline preceding the onset of the QRS complex. In contrast, FIG. 4 shows the ST segment elevated relative to the isoelectric baseline, in this example, by 5 mm. The serial comparison program detects any change in the ST segment elevation, as well as the appearance of a new Q wave. These are not normal variations, but rather are treated as indicative of possible acute myocardial infarction (AMI). The evolution of AMI is depicted in FIG. 5, with a small change in ST segment elevation being indicated by reference numeral 22 and a small new Q wave being indicated by reference numeral 24.

Figure 6:
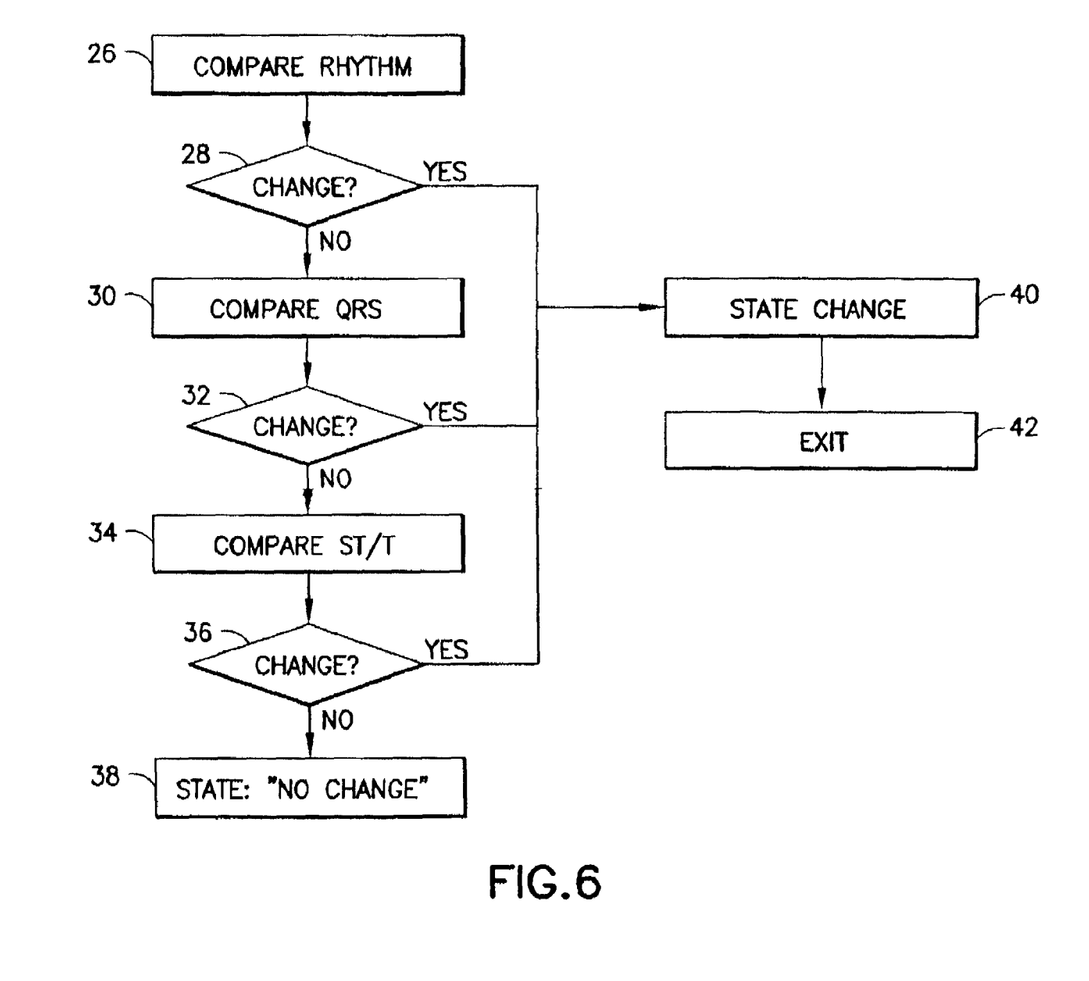
FIG. 6 is a flowchart showing the serial comparison process.

The algorithm performed by the serial comparison program is shown in FIG. 6. In step 26, the dominant rhythms (sinus, ventricular, etc.) are compared using diagnostic statements contained in the current and previous electrocardiogram records. Rhythm modifiers are compared only if the dominant rhythm has not changed. The diagnostic statements are used to detect major changes (step 28) in rhythm that would result in a change in the QRS complex. If a major (i.e., clinically significant) change in rhythm has occurred, the change is stated (step 40) and then the computer exits the serial comparison program (step 42). If no major change in rhythm has occurred, then the QRS complexes for the respective electrocardiograms are compared using statements, measurements and waveform analysis (step 30) for the purpose of detecting conduction and infarction. Changes in the axis and voltage (amplitude) are also detected. Based on the comparison, the serial comparison program determines a change indicative of infarction has occurred (step 32). If "Yes", then the change is stated (step 40). If "No", the standard ST/T analysis using waveforms is performed (step 34). The ST/T analysis looks for the presence/absence of acute myocardial infarction or ischemia. For example, the ST/T analysis looks for an increase in elevation of the ST segment in the waveform for the current electrocardiogram. If the criteria for detection of infarction are met, the change is stated (step 40). If the criteria for detection of infarction are not met, then a statement that no change has occurred is generated in the serial comparison report.

Figure 7:
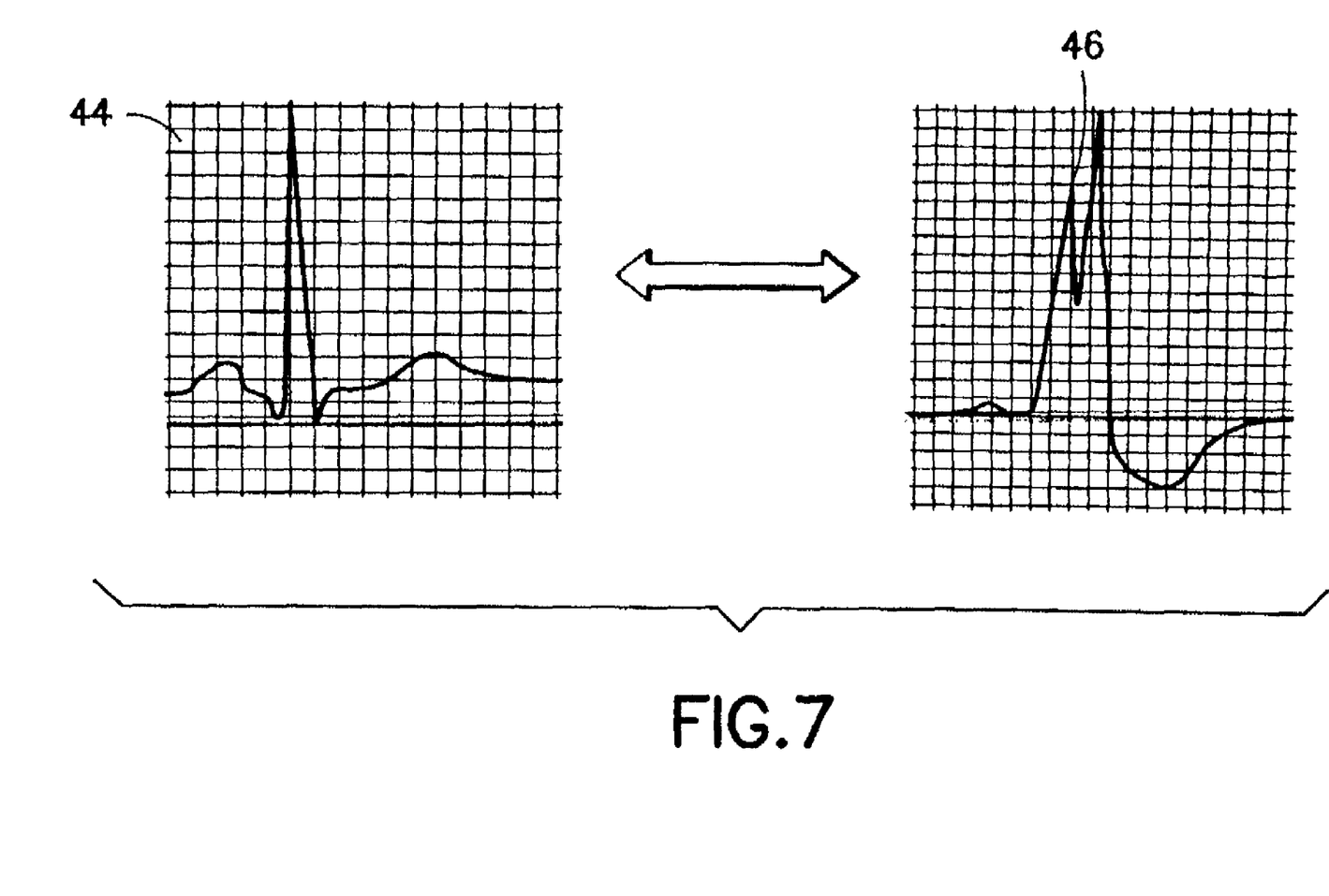
FIG. 7 is a schematic comparing a normal ECG waveform with an LBBB ECG waveform.

An example of a waveform acquired from the V5 lead and having a normal QRS complex is depicted on the left-hand side of FIG. 7. An example of a waveform acquired from the V5 lead and having a QRS complex typical for a left bundle branch block is depicted on the right-hand side of FIG. 7.

In accordance with the preferred embodiments of the invention, the current ECG indicates that a patient is suspected of or has a high probability of acute myocardial infarction. The system can be configured such that all ECGs acquired from a certain location (such as an emergency department chest pain clinic) can be treated as "suspect acute myocardial infarction". Alternatively, patient symptoms or the reason for testing can be directly entered into the ECG record at the electrocardiograph cart. The serial comparison program then senses the "suspect acute myocardial infarction" status of the current ECG record and implements new code within the QRS analysis module.

Figure 8:
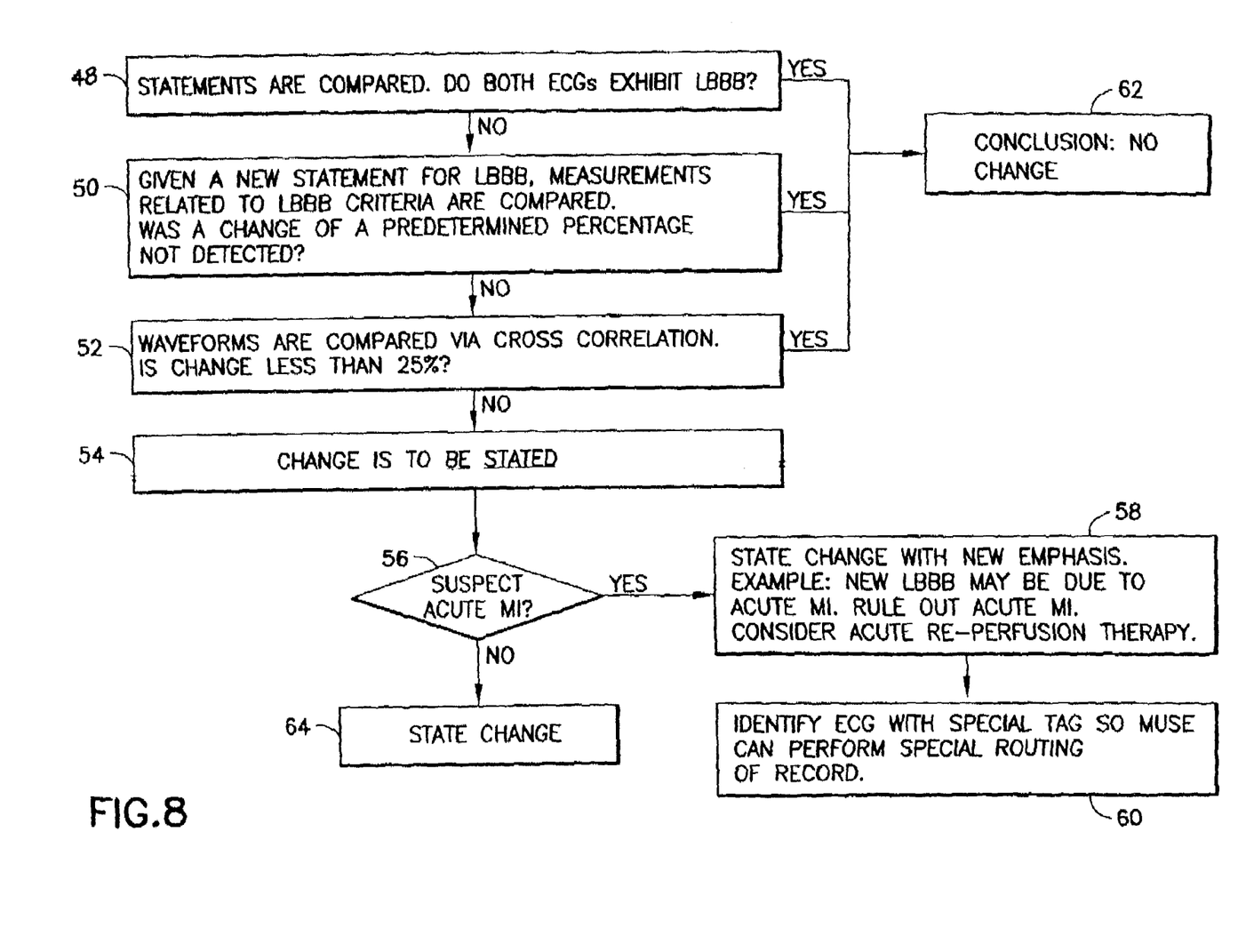
FIG. 8 is a flowchart showing a serial comparison process in accordance with the preferred embodiment of the invention.

The QRS analysis module of the serial comparison program is modified as shown in FIG. 8. In accordance with the preferred embodiments, each current ECG record is compared with a previous ECG record for the same patient (step 48). First, the diagnostic statements for the two ECG records are compared. If both ECGs exhibit LBBB, then no change is stated in the serial comparison report (step 62), i.e., the detected LBBB is not new. However, if only the current ECG record includes a diagnostic statement indicating LBBB, then the algorithm proceeds to the next step. In step 50, measurements related to LBBB criteria are compared. If changes of a predetermined percentage are not present, then no change is stated (step 62). If changes of a predetermined percentage are present, then the algorithm compares the ECG waveforms using cross correlation (step 52). If the change in the current waveform is less than a predetermined percentage, e.g., less than 25%, then no change is stated (step 62). Conversely, if the change in the current ECG waveform, compared to the previous ECG waveform, is greater than 25%, then a determination is made (step 54) that the change will be stated in the serial comparison report.

The system then automatically determines whether the patient belongs to the category comprising patients identified to have a high probability of acute myocardial infarction (step 56). If acute myocardial infarction is not suspected, the system generates a diagnostic statement stating the change (step 64) in the serial comparison report. Alternatively, if acute myocardial infarction is suspected, the system generates a diagnostic statement (step 58) stating that the new left bundle branch block may be due to acute myocardial infarction. The diagnostic statement may further instruct the reader to "Rule out acute MI. Consider acute re-perfusion therapy". The current ECG record exhibiting a new LBBB is then identified with a special tag (step 60) and sent to a central database server of the MUSE® system. The MUSE® system then uses this special tag to perform special routing of the current ECG record, e.g., via facsimile or digital pager, to alert on-call medical personnel to the need for immediate treatment.

Figure 9:
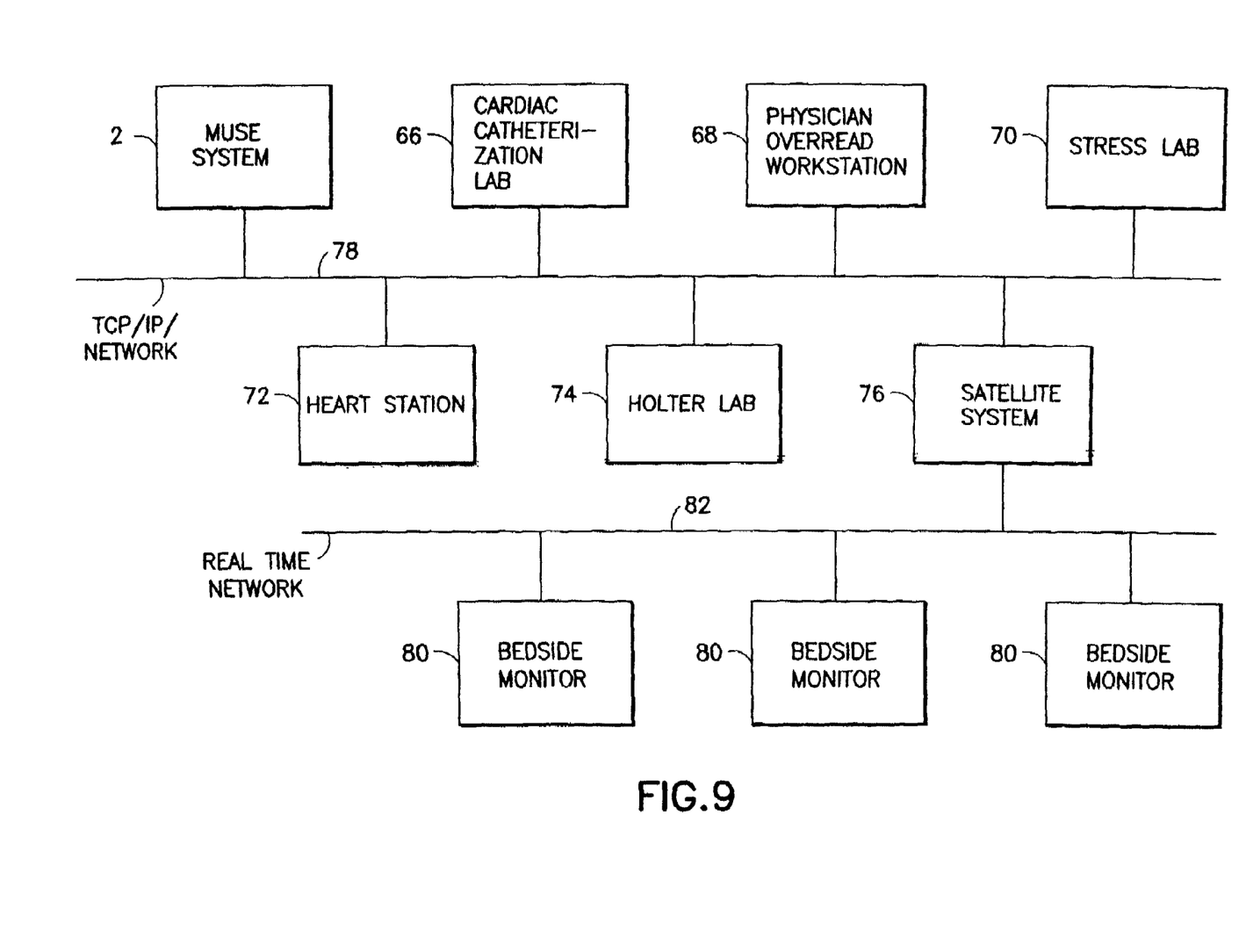
FIG. 9 is a block diagram showing a cardiovascular information network having a satellite system for detecting changes in ECGs acquired by bedside patient monitors in accordance with the preferred embodiment of the invention.

FIG. 9 generally depicts one possible configuration for an integrated system installed in a hospital or other health care facility. The MUSE® ECG management system 2 communicates with other departments and stations in the hospital via a TCP/IP network 78. For the purpose of illustration, FIG. 9 shows a cardiac catheterization lab 66, a physician overread workstation 68, a stress lab 70, a heart station 72, and a Holter lab 74, all of which are well known in the art. It is also known in the art to provide a satellite system 76 which communicates with the MUSE® system 2 via the TCP/IP network 78. The satellite system 76 typically comprises a computer programmed to receive and analyze ECG records transmitted from a plurality of bedside monitors 80 via a real-time local area network 82. The bedside monitors 80 continuously monitor patients. The patients are typically located in a coronary care unit, emergency department or chest pain clinic. The satellite system 76 acquires 12-lead ECGs every minute from the monitors and trends the results. If measurements change above a predetermined threshold, an alert is generated. The acquired ECG records are sent by the satellite system 76 to the MUSE® system via the network 78. The MUSE® system also receives a final report of trends from the satellite system. The MUSE® system generates reports and sends those reports to other devices and systems. Conventional routing software uses several identifiers for routing reports, such as location, report status, and normal/abnormal.

In accordance with the preferred embodiment of the invention, the computer of the satellite system 76 is programmed to perform serial analysis on the ECG records continuously acquired from the bedside monitors 80. The previous ECG records for monitored patients are retrieved from the central ECG database of the MUSE® system 2.

In accordance with one preferred embodiment, the computer of the satellite system is programmed to request and receive a previous electrocardiogram record for each patient from the central database; receive the current electrocardiogram record for each patient from a respective bedside monitors; and determine whether a new left bundle branch block is present in each patient based on a comparison of data in the current and previous electrocardiogram records. The details of the determining step are shown in FIG. 8 and will not be described again. If it is determined that a new LBBB is present for any patient, the computer generates a diagnostic statement or an alert indicating that that the new left bundle branch block may be due to acute myocardial infarction. In response to the alert, expedited treatment for acute myocardial infarction can be provided.

In accordance with a further aspect of the invention, a specific routing tag is added to the current ECG record based on the automated diagnosis of a new LBBB. The satellite system 76 then sends the current ECG record to the MUSE® system via the network 78. The special routing tag in the transmitted current ECG record enables the MUSE® system to perform special routing of the current ECG record.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

As used in the claims, the terms "current" and "previous" are used to refer to electrocardiogram records which were acquired at different times, the "current" electrocardiogram record being acquired at a time subsequent to the time when the "previous" electrocardiogram record was acquired.

What is claimed is:

1. A method for monitoring a patient for the presence of a new bundle branch block, comprising the steps of:
    acquiring current and previous electrocardiogram records at different times for a particular patient;
    determining that a new bundle branch block is present in said particular patient based on an automated comparison of data in said current and previous electrocardiogram records;
    automatically detecting that said particular patient belongs to a category of patients comprising patients identified to have a high probability of acute myocardial infarction; and
    automatically generating a diagnostic statement stating that the new bundle branch block may be due to acute myocardial infarction,
    wherein said automated comparison comprises the following steps:
    determining that said current electrocardiogram record comprises a diagnostic statement indicating the presence of a bundle branch block and determining that said previous electrocardiogram record does not comprise a diagnostic statement indicating the presence of a bundle branch block;
    computing a percentage change in a measurement relating to a bundle branch block criterion in said current and previous electrocardiogram records; and
    determining that said percentage change exceeds a first predetermined threshold.

2. The method as recited in claim 1, further comprising the step of automatically tagging said current electrocardiogram record with a special tag.

3. The method as recited in claim 2, wherein said tagging step is performed by a satellite system connected to a network, further comprising the step of sending said specially tagged current electrocardiogram record to a central database via said network.

4. The method as recited in claim 1, wherein said automated comparison further comprises the steps of:
    computing a correlation value for respective waveforms in said current and previous electrocardiogram records using cross correlation; and
    determining that said correlation value exceeds a second predetermined threshold.

5. A system for monitoring a patient for the presence of a new bundle branch block, comprising:
    means for acquiring current and previous electrocardiogram records at different times for a particular patient;
    means for determining whether a new bundle branch block is present in said particular patient based on a comparison of data in said current and previous electrocardiogram records;
    means for detecting whether said particular patient belongs to a category of patients comprising patients identified to have a high probability of acute myocardial infarction, said detecting means being operative if said determining means have determined that a new bundle branch block is present; and
    means for generating a diagnostic statement stating that the new bundle branchblock may be due to acute myocardial infarction, said generating means being operative if said detecting means have detected that said particular patient belongs to said category,
    wherein said determining means comprise a computer programmed to determine which of said current and previous electrocardiogram records contain a diagnostic statement indicating the presence of a bundle branch block, and to perform the following steps if said current electrocardiogram record contained a statement indicating the presence of a bundle branch block and said previous electrocardiogram record did not contain a statement indicating the presence of a bundle branch block:
    computing a percentage change in a measurement relating to a bundle branch block criterion in said current and previous electrocardiogram records; and
    comparing said percentage change to a first predetermined threshold.

6. The system as recited in claim 5, further comprising means for tagging said current electrocardiogram record with a special tag if said detecting means have detected that said particular patient belongs to said category.

7. The system as recited in claim 6, further comprising a network and a central database connected to said network, wherein said determining means, said detecting means, said generating means and said tagging means comprise programming executed by a computer connected to said network, said programming further comprising a routine for sending said specially tagged current electrocardiogram record from said computer to said central database via said network.

8. The system as recited in claim 5, wherein said determining means further comprise said computer programmed to perform the following steps if said percentage change exceeded said first predetermined threshold:
    computing a correlation value for respective waveforms in said current and previous electrocardiogram records using cross correlation; and
    comparing said correlation value to a second predetermined threshold.

9. The system as recited in claim 8, wherein said detecting means comprise said computer programmed to detect whether said particular patient is suspected to have suffered acute myocardial infarction if said correlation value exceeded said second predetermined threshold.

10. The system as recited in claim 5, wherein said detecting means detect that said particular patient belongs to said category by recognizing that said current electrocardiogram was acquired from a hospital unit for patients suspected to have acute myocardial infarction.

11. The system as recited in claim 5, wherein said detecting means detect an indicator included in said current electrocardiogram, said indicator identifying a symptom indicative of suspected acute myocardial infarction.

12. A system for monitoring a patient for the presence of a new bundle branch block, comprising:
- memory for storing a previous electrocardiogram record;
- an instrument for acquiring a current electrocardiogram record at a time which is later than the time when said previous electrocardiogram record was acquired; and
- a computer programmed to perform the following steps:
- determining whether a new bundle branch block is present in said particular patient based on a comparison of data in said current and previous electrocardiogram records;
- detecting whether said particular patient belongs to a category of patients comprising patients identified to have a high probability of acute myocardial infarction, said detecting step being performed if a determination has been made that a new bundle branch block is present; and
- generating a diagnostic statement stating that the new bundle branch block may be due to acute myocardial infarction, said generating step being performed if membership of said particular patient in said category has been detected,
- wherein said determining step comprises the step of determining which of said current and previous electrocardiogram records contain a diagnostic statement indicating the presence of a bundle branch block, and further comprises the following steps, which are performed if said current electrocardiogram record contained a statement indicating the presence of a bundle branch block and said previous electrocardiogram record did not contain a statement indicating the presence of a bundle branch block:
  - computing a percentage change in a measurement relating to a bundle branch block criterion in said current and previous electrocardiogram records; and
  - comparing said percentage change to a first predetermined threshold.

13. The system as recited in claim 12, wherein said instrument comprises a bedside monitor in a coronary care unit, emergency department or chest pain clinic, further comprising a local area network connecting said computer to said bedside monitor.

14. The system as recited in claim 12, wherein said computer is further programmed to tag said current electrocardiogram record with a special tag if said detecting step has detected that said particular patient belongs to said category.

15. The system as recited in claim 14, further comprising a central database and a network connecting said computer to said central database, wherein said computer is further programmed to send said specially tagged current electrocardiogram record to said central database via said network.

16. The system as recited in claim 12, wherein said determining step further comprises the following steps, which are performed if said percentage change exceeded said first predetermined threshold:
- computing a correlation value for respective waveforms in said current and previous electrocardiogram records using cross correlation; and
- comparing said correlation value to a second predetermined threshold.

* * * * *